US012736549B2

(12) United States Patent
Carew

(10) Patent No.: US 12,736,549 B2
(45) Date of Patent: Sep. 15, 2026

(54) MINIMAL SURFACE AREA COLLECTION DEVICE AND RAPID METHOD FOR ESTIMATING LOW BLOOD VOLUME

(71) Applicant: CYPHER MEDICAL, LLC, Boerne, TX (US)

(72) Inventor: Christopher A. Carew, Fair Oaks Ranch, TX (US)

(73) Assignee: CYPHER MEDICAL, LLC, Boerne, TX (US)

( * ) Notice: Subject to any disclaimer, the term of this patent is extended or adjusted under 35 U.S.C. 154(b) by 1078 days.

(21) Appl. No.: 17/782,597

(22) PCT Filed: Dec. 3, 2020

(86) PCT No.: PCT/US2020/063083
§ 371 (c)(1),
(2) Date: Jun. 3, 2022

(87) PCT Pub. No.: WO2021/133532
PCT Pub. Date: Jul. 1, 2021

(65) Prior Publication Data

US 2023/0008808 A1 Jan. 12, 2023

Related U.S. Application Data

(60) Provisional application No. 62/944,752, filed on Dec. 6, 2019.

(51) Int. Cl.
*G01N 33/80* (2006.01)
*G01N 1/10* (2006.01)

(52) U.S. Cl.
CPC ............... *G01N 33/80* (2013.01); *G01N 1/10* (2013.01)

(58) Field of Classification Search
CPC ................................ G01N 33/80; G01N 1/10
See application file for complete search history.

(56) References Cited

U.S. PATENT DOCUMENTS 8,951,780 B2 2/2015 Ruhstorfer et al.
2004/0044315 A1 3/2004 Ward, Jr.
(Continued)

FOREIGN PATENT DOCUMENTS

CN 206399701 U 8/2017
CN 208254921 U 12/2018
CN 209360703 U * 9/2019

OTHER PUBLICATIONS

Supplementary European Search Report dated Nov. 20, 2023, in related European patent application No. EP 20 90 4627, 9 pages.

*Primary Examiner* — Charles Capozzi
*Assistant Examiner* — Alex Ramirez
(74) *Attorney, Agent, or Firm* — Munck Wilson Mandala LLP; Denise L. Mayfield

(57) ABSTRACT

An insert for a holding device for reliably and accurately assessing a small volume of blood in a fluid, such as in a volume of surgical fluid collected during a surgical procedure, is provided. The insert may include a circular shelf having an outside perimeter configured to fit up against an inside perimeter of a holding device. The insert may include a center opening. The insert may include a conically-shaped collection cone disposed in the center opening. The collection cone may include a length, an interior surface comprising a red blood cell flocculant coating, a gradually decreasing perimeter terminating in a bottom apex, and a series of graduated volumetric markings along the length of the collection cone.

7 Claims, 8 Drawing Sheets

(56) References Cited

U.S. PATENT DOCUMENTS

| | | | | |
|---|---|---|---|---|
| 2010/0021351 | A1* | 1/2010 | Hollander | B01L 3/502<br>422/400 |
| 2018/0196031 | A1* | 7/2018 | Carew | G01N 9/02 |
| 2019/0154658 | A1 | 5/2019 | Carew et al. | |

* cited by examiner

MINIMAL SURFACE AREA COLLECTION DEVICE AND RAPID METHOD FOR ESTIMATING LOW BLOOD VOLUME

CROSS-REFERENCE TO RELATED APPLICATIONS

The present application is a National Stage filing based upon International Application No. PCT/US2020/063083, filed Dec. 3, 2020, which claims the benefit of priority to U.S. Provisional Patent Application Ser. No. 62/944,752, filed Dec. 6, 2019, all of which are incorporated herein in their entirety.

BACKGROUND OF THE INVENTION

During surgery, blood, saline, and in some cases, small tissue are evacuated from a subject's body, and collected in a collection device. Typically, this evacuation process is accompanied by suction. The components in the collection device include at least some volume of blood in most cases. However, the volume of blood included is difficult to assess with any degree of accuracy. Blood loss assessment is critical to the health of the subject, but currently is assessed by only crude techniques associated with the counting of saline units employed during the surgical procedure by the attending health care professional/anesthesiologist. At the conclusion of the surgery, typically the anesthesiologist will estimate the amount of blood lost by determining what volume of saline was used during the surgery overall, and then subtracting this saline volume from the total volume of mixed material collected in the collection canister(s).

Blood is composed of red blood cells (RBCs), and RBCs require a significant amount of time (over 3-6 hours) to settle out of a blood/fluid mixture collected at the time of surgery. Apart from the significant time required to provide even a reading of settled RBC volume, it has been found that the settled RBC volume does not provide an adequate approximation of blood volume for assessing blood needs. Current techniques for estimating blood loss are fraught with challenges, including human error (counting "used" saline bags, accounting for residual saline) and serious time constraints associated with conventional blood-containing fluid analysis.

The medical arts remain in need of improved techniques and materials to accurately estimate blood loss. Methods for more accurately monitoring and approximating blood volume in a fluid are needed. Fluid collection products suitable for providing a more accurate blood volume approximation are also needed, as will serve to reduce medical costs associated with unnecessary medical treatments and interventions that occur as a result.

SUMMARY OF THE INVENTION

In a general and overall sense, the present invention provides materials, devices and methods for more reliably and accurately approximating very low blood volume levels, such as detecting small amounts of blood in a liquid collected during a surgical procedure.

Within this disclosure, it should be understood that the characterization of red blood cell (RBC) volume separated from a fluid or other material, suspected to contain blood plasma, saline or any other fluid (e.g., urine), does not mean an absolute or total separation, but instead an approximation of the stable sedimentation of RBCs in the fluid. RBC sedimentation is to be assessed at room temperature, and relates to the settlement of RBCs in a sample liquid or other material by gravity (no centrifugation), and at room temperature, within about 5 minutes to less than 10 minutes from time of collection of a sample.

According to one aspect, the invention provides a collection device configured for assessing blood volume in a material. In some embodiments, the collection device comprises an enclosed perimeter sidewall having an upper edge and a lower edge and defining an interior space located therein, a bottom panel extending across said lower edge of said sidewall, an insert positioned within said interior space, the insert comprising an upper divider wall engaging said perimeter sidewall and a conical-shaped collection reservoir having a gradually decreasing volume beginning at an upper opening defining a top most larger perimeter decreasing in size to an apex having a smaller perimeter, and a graduated marking along a vertical wall provided on a vertical surface corresponding to a volumetric measure of settled material within the conical-shaped collection reservoir. In a particular embodiment, the graduated marking is provided along an outer wall or inner wall of the conical-shaped collection reservoir.

According to another aspect, a method of using the collection device that allows for the accurate and rapid approximation of very small amounts of blood in a liquid or other material is provided According to one embodiment, the collection device configured for receiving fluids, including blood plasma and other fluids evacuated from a patient during surgery or other medical procedures. The collection device may include a perimeter or peripheral sidewall and top and bottom walls defining an interior space or volume therein. The collection device may have any suitable shape or form, including cylindrical as described herein, or any other suitable form, such as without limitation, round, square, octagonal, conical or virtually any configuration. The collection device may be sufficiently transparent or at least opaque so as to permit the visual detection of a level of material, such as sedimented RBCs, within the collection device. The collection device may be constructed from or comprise any suitable material or materials. According to certain embodiments, the collection device can be of a solid or flexible material, such as a hard plastic or glass, or a plastic material. The collection device further may include a series of volumetric demarcations associated with the volume of the device itself.

Within the interior volume, the collection device may include a lower sectional component or insert with a conical-shaped cavity to collect fluid that may contain blood. The collection device may also include graduated markings (e.g., 3 ml, 6 ml, 9 ml, 12 ml, 15 ml, etc.) associated with the conical-shaped cavity to indicate the amount of blood and/or other fluids that have been collected therein. When blood and other fluid(s) are collected into the collection device (such as during surgery or another type of medical procedure), RBCs may sediment down to the bottom of the device and into the conical-shaped cavity. This can allow the amount of blood loss from the patient during the surgery or medical procedure to be easily identified and detected. Further, the conical-shaped cavity within the collection device may allow for very minimal amounts of blood to be detected and/or measured therein (such as, for example, blood amounts approximately as small as 3 ml).

According additional embodiments, the present invention is directed toward methods of using the collection device to approximate blood volume in a liquid. The methods of the present invention may be utilized with the collection device in connection with the teachings and/or methods described in U.S. Pat. No. 10,401,347 to Carew et al., entitled "Method of Estimating Blood Volume," the entire disclosure of which is incorporated herein by reference.

The methods for using the collection device of the present invention may be configured to measure blood loss from a mammal, such as a human or veterinary animal, using an RBC flocculant in connection with the collection device. The use of an RBC flocculant may reduce the total amount of time required for sedimentation of the RBCs within the liquid contained within the collection device and thereby allow for faster determination of a blood loss approximation. The method in some embodiments comprises providing a liquid in the collection device having therein an RBC flocculant, wherein the RBCs within blood contained in the liquid will sediment to permit a visual and essentially simultaneous RBC sedimentation volume. While settled RBC volume does not necessarily equate to blood volume in a liquid, the RBC sedimentation volume may be used to approximate blood volume in the liquid. The method may employ an RBC sedimentation volume observed in the presence of an RBC flocculant, the aspect ratio of the collection device and an average hematocrit, to provide a visually ascertainable approximation of blood volume in the liquid.

The visually ascertainable approximation of blood volume in a liquid/fluid containing or possibly containing blood using the collection device and methods described herein may be achieved in less than an hour, and as quickly as within 15-30 minutes, using the collection device and techniques described herein. The very short time frame facilitated for providing RBC sedimentation in the presence of an RBC flocculant, and the consequent visual assessment of approximate blood volume, provides significant advantages in maintaining the well-being of the patient, as well as significant resource savings to the health care provider.

According to one embodiment, the methods of using the collection device may also be used to detect the presence of blood in a liquid, and in this manner, may be used to test a material (such as food materials, water, pharmaceuticals, etc.) for the presence of blood contamination. The material in question would be placed in contact with a RBC flocculant provided within the collection device and examined for presence of RBC sedimentation. RBC sedimentation would indicate the presence and amount of blood in the material.

Any suitable flocculant now known or hereinafter developed may be used in connection with the methods and collection device of the present invention, including without limitation, the flocculants described in detail in U.S. Pat. No. 10,401,347. Such flocculants are preferably suitable for flocculating RBCs and thereby facilitating the sedimentation of RBCs by gravity. Combined with a biological fluid, such as the aspirate or other surgical run off collected during a surgical or other medical procedure episodes, the RBC flocculant may facilitate the rapid sedimentation of RBCs within a mixed fluid, such as within about 15 to about 30 minutes, compared to several hours that would otherwise be required for RBCs in a fluid to settle in the absence of an RBC flocculant (however, it is recognized that collection device may be suitably used without a flocculant in certain applications). As used in the description of the present invention, flocculation may be defined as the coalescence or formation of clusters of RBCs within a fluid comprising blood or potentially comprising blood. The collection device and methods of the present invention may therefore be used to detect blood contamination, as well as to quantify an amount of blood in a material by providing for the detection of RBCs in the material and the approximation of blood volume according to the methods disclosed herein.

Fluids potentially comprising blood and utilized in connection with the collection device and methods of the present invention may include saline, surgical aspirate, urine, bile, other biological waste materials, saliva, tissue preparations, digestive fluids, cerebral fluids, lymph, peritoneal fluid, amniotic fluid, and any mixture or combination of these. In this regard, virtually any moiety or chemical agent that is capable of promoting the coalescence of RBCs within less than about 30 minutes at room temperature to provide a stable settled RBC level is considered useful as an RBC flocculant for purposes of providing the present devices and for use in the present methods. It is envisioned that virtually any moiety or chemical entity that may impart a positive surface charge to a negatively charged RBC would be useful to promote a more rapid coalescence or flocculation of RBCs together sufficient to enhance the speed of RBC sedimentation as part of the present devices and methods.

RBCs present in a fluid containing blood become bound to each other in the presence of an RBC flocculant, and in this manner form heavier particles that settle within the collection device when provided therein, and particularly within the conical-shaped cavity providing in the collection device. Once the RBCs settle, the volume of the settled RBCs may be recorded and employed together with a predetermined hematocrit of the mammal (animal/human), and a calculated RBC packing ratio associated with the collection vessel, so as to provide a real-time estimate of approximate blood volume in a liquid or mixed collected specimen.

Virtually any material or chemical may be used as an RBC flocculant in the practice of the present invention, as long as the material is able to facilitate the aggregation of RBCs to one another and decrease the time the RBCs aggregate and form a stable sedimentation level, preferably within about 15 minutes. The amount of RBC flocculant should be sufficient to facilitate the stable sedimentation of RBCs present in a fluid within less than about 60 minutes. In some embodiments, the amount of RBC flocculant should be an amount sufficient to facilitate a stable sedimentation of RBCs in a fluid within about 5 minutes, about 10 minutes, about 15 minutes, about 20 minutes, about 25 minutes or within about 30 minutes, or within a time range of about 5 minutes to about 20 minutes, at room temperature and in the absence of centrifugation. The amount of the RBC flocculant should be sufficient to impart a cationic charge to surfaces of RBCs in a liquid, such as a liquid comprising blood. The RBC flocculant may be provided in the collection device as a dry weight amount of flocculant, or as an amount of flocculant in a carrier solution, or as a pre-coating on the collection device (such as evenly coated on at least one surface, the entire surface, on a partial area, or as a strip along the inside of the device). These descriptions are provided by way of example and are not intended to provide limitation of potential embodiments envisioned for use and practice of the present collection devices and methods.

According to the methods of the present invention, after RBCs are settled within the conical-shaped cavity of the collection device (which may include an RBC flocculant), a settled RBC volume can be estimated using graduated markings on the collection device and associated with the conical-shaped cavity.

As described herein, the present invention is directed toward methods of using the collection device to estimate blood volume in a liquid. In particular embodiments, the method is used to estimate blood volume loss from a patient from fluid collected during a surgical procedure. The method includes collecting a volume of liquid into the collection device that includes an RBC flocculant suitable for imparting a relatively positive charge to the surface of an RBC, for a period of time sufficient to permit RBC sedimentation by gravity within the collection device.

The volume of sedimented RBCs after a sufficient period of time, together with an estimated hematocrit of the type of animal/human blood in the fluid, is used together with a calculated RBC packing ratio determined for the particular collection device, to calculate an approximate blood volume value in the liquid collected. Alternatively, these calculations are provided in a calibrated marking panel called a Blood Indicator Panel (BIP), as part of the present invention, which may be included on the collection device. As such, an immediate and visual blood volume assessment may be provided as RBCs in fluid collected in the flocculant containing collection device sediments. In some embodiments, the BIP will include a calibrated marker coinciding to an estimated blood volume (e.g., 50 ml, 100 ml, 200 ml, 400 ml, and 600 ml), and a volumetric alignment marking for aligning the BIP within a conventionally volumetrically marked conical-shaped cavity within the fluid collection device (e.g., 5 ml, 10 ml, for example), such as is common on a conventional 1200 ml canister.

The invention is also directed to a kit or system that includes the collection device with an appropriate amount of an RBC flocculant provided therein and calibrated with blood volume demarcations, a first length of tubing suitable for aspirating a fluid from an area into a first port on the receptacle, a second length of tubing suitable for connecting with a source of suction and a second port of the receptacle, so as to impart a vacuum in the receptacle. The system may be provided as a kit, and may also include an instructional insert.

Other aspects and advantages of the present invention will be apparent from the following detailed description of the preferred embodiments of the accompanying drawing figures.

DESCRIPTION OF THE SEVERAL VIEWS OF THE DRAWING

In the accompanying drawing, which forms a part of the specification and is to be read in conjunction therewith in which like reference numerals are used to indicate like or similar parts in the various views.

DETAILED DESCRIPTION OF THE INVENTION

Figure 1:
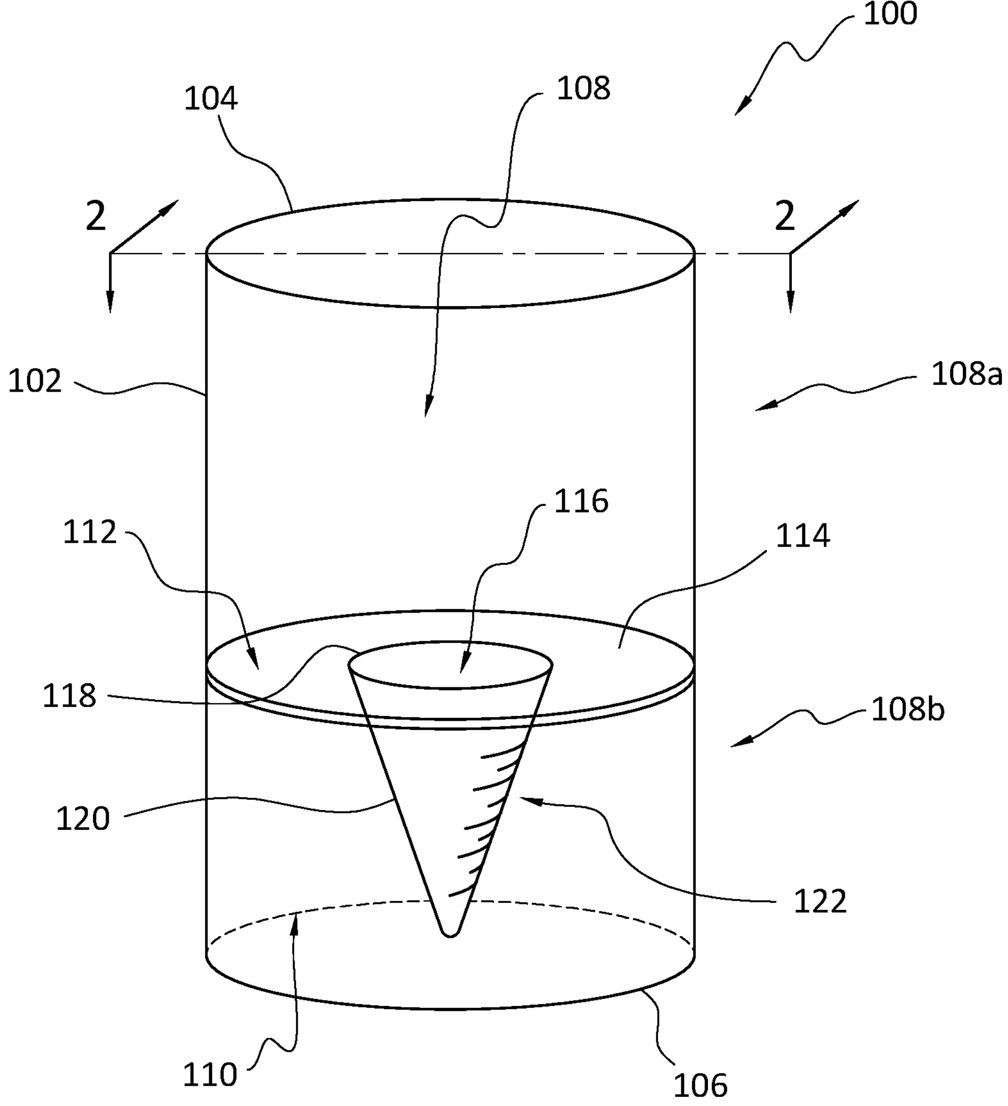
FIG. 1 is a schematic perspective view of a collection device for determining the amount of blood volume within a volume of liquid in accordance with one embodiment of the present invention.

The invention will now be described with reference to the drawing figures, in which like reference numerals refer to like parts throughout. For purposes of clarity in illustrating the characteristics of the present invention, proportional relationships of the elements have not necessarily been maintained in the drawing figures.

The following detailed description of the invention references specific embodiments in which the invention can be practiced. The embodiments are intended to describe aspects of the invention in sufficient detail to enable those skilled in the art to practice the invention. Other embodiments can be utilized and changes can be made without departing from the scope of the present invention. The present invention is defined by the appended claims and the description is, therefore, not to be taken in a limiting sense and shall not limit the scope of equivalents to which such claims are entitled.

Unless defined otherwise, all technical and scientific terms used herein have the same meaning as commonly understood by one of skill in the art to which the disclosure pertains. Although any methods and materials similar to or equivalent to those described herein can be used in the practice or testing of the present technology, the preferred methods and materials are described herein.

As used here, the term "flocculant" is intended to mean a molecule that has a cationic charge that is capable of facilitating the coalescence of RBCs in a fluid at room temperature, and form a settled RBC mass with less than 30 minutes at room temperature without centrifugation.

Reference to an element by the indefinite article "a" or "an" does not exclude the possibility that more than one element is present, unless the context clearly requires that there be one and only one element. The indefinite article "a" or "an" thus usually means "at least one."

As used herein, "patient" or "subject" means an individual having symptoms of, or at risk for, cancer or other malignancy. A patient may be human or non-human and may include, for example, animal such a horse, dog, cow, pig or other animal. Likewise, a patient or subject may include a human patient including adults or juveniles (e.g., children). Moreover, a patient or subject may mean any living organism, preferably a mammal (e.g., human or non-human) from whom a blood volume is desired to be determined and/or monitored from the administration of compositions contemplated herein.

As used herein, "about" means within a statistically meaningful range of a value or values such as a stated concentration, length, molecular weight, pH, sequence identity, timeframe, temperature or volume. Such a value or range can be within an order of magnitude, typically within 20%, more typically within 10%, and even more typically within 5% of a given value or range. The allowable variation encompassed by "about" will depend upon the particular system under study, and can be readily appreciated by one of skill in the art.

The following examples are presented to demonstrate preferred embodiments of the invention.

Example 1—Novel Low Blood Volume Collection Device with Conical-Shaped Cavity (Reservoir)

With reference to the figures, the present invention is directed to a collection device 100 configured for reliably and accurately approximately very low blood volume levels, such as detecting small amounts of blood in a liquid collected during a surgical procedure, and enabling visual estimation of blood loss. FIGS. 1-7 schematically illustrate collection device 100 with a cylindrical shape in accordance with selected embodiments of the present invention. It is also recognized that collection device 100 may have any other suitable shape and configuration in alternative embodiments not specifically disclosed herein.

Figure 4:
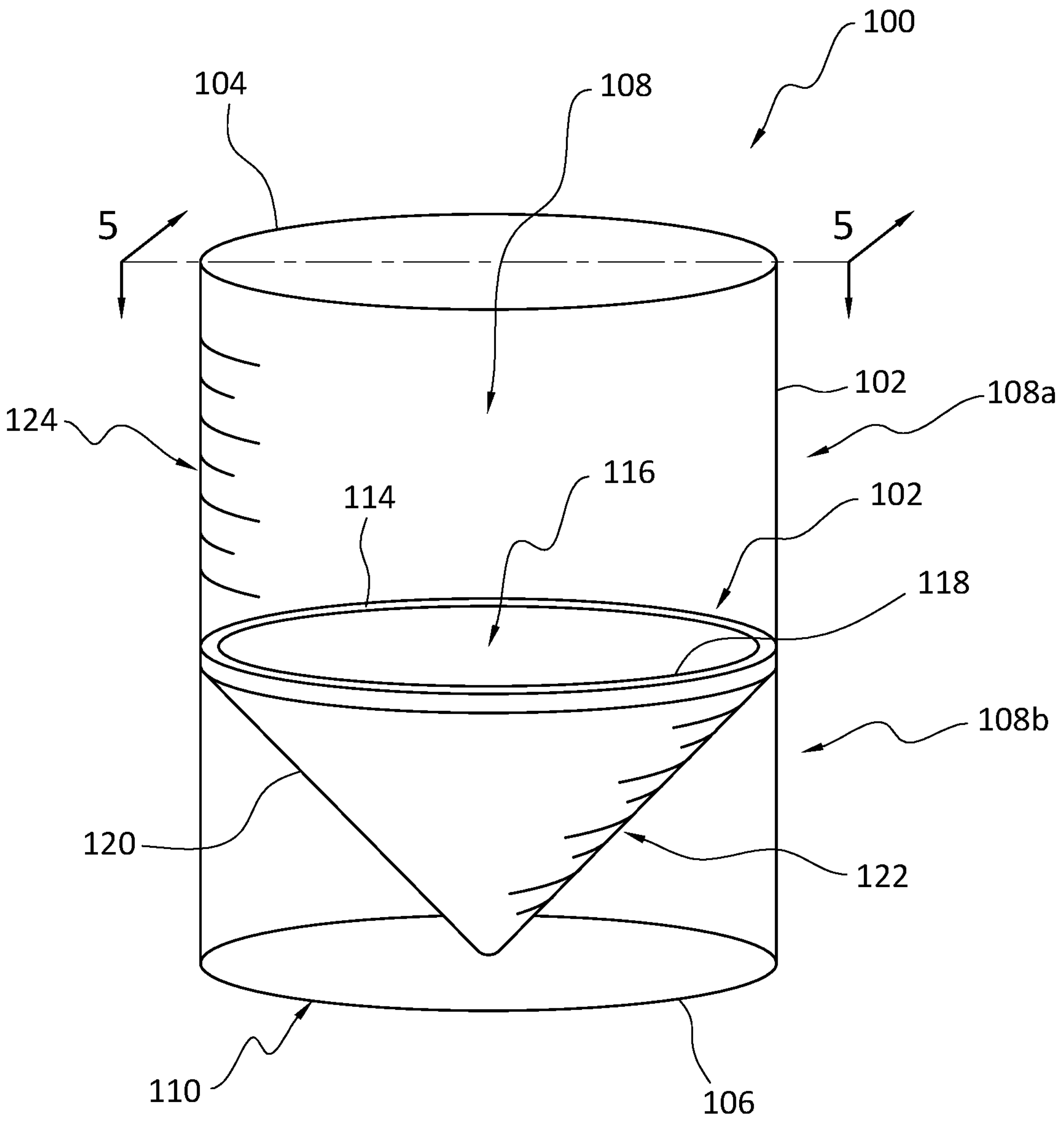
FIG. 4 is a schematic perspective view of a collection device for determining the amount of blood volume within a volume of liquid in accordance with another embodiment of the present invention.
Figure 7:
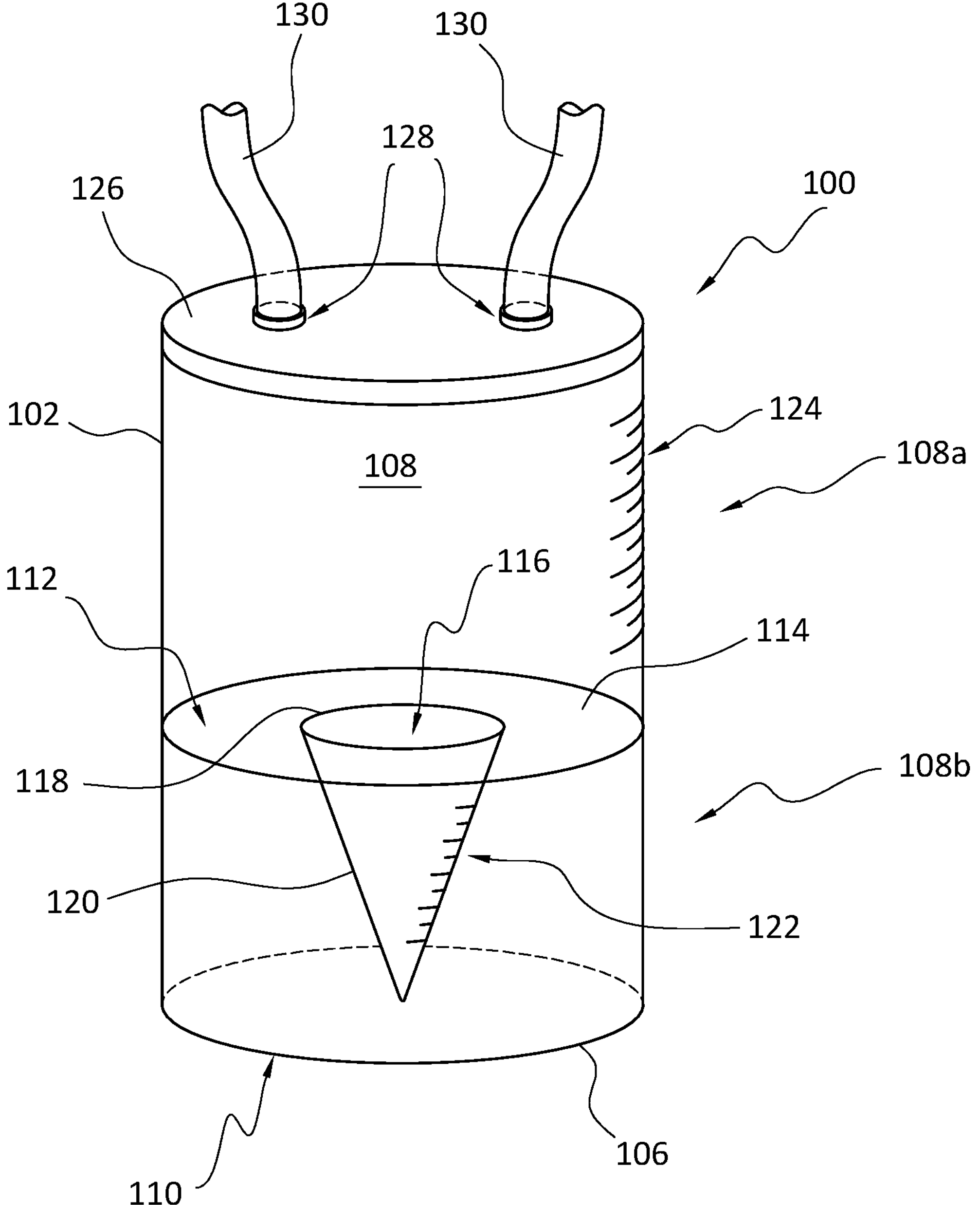
FIG. 7 is a schematic perspective view of a collection device for determining the amount of blood volume within a volume of liquid in accordance with yet another embodiment of the present invention.

As best shown in FIGS. 1 and 4, collection device 100 may be further described as a conical collection device. The conical collection device 100 may include an enclosed perimeter sidewall 102, the sidewall 102 being configured to provide a holding device **108*b* suitable for securing the conical-shaped fluid collection cone 120 within the shelf 114 of the conical collection device 100 (See FIG. 1). The conical shaped fluid collection cone 120 will have a length, an upper edge 118 configured to fit within the opening of the shelf, and a lower edge 106 defining an interior space or void 108 within collection device 100. Collection device 100 may further include a bottom disc or panel 110 enclosing the lower end of collection device 100 and interior space 108. Bottom panel 110 can have a circular shape and can be secured to lower edge 106 of sidewall 102 or integrally formed with sidewall 102 depending on the particular configuration. As best shown in FIG. 7, collection device 100 may additionally include an upper panel or lid 126 that can selectively enclose the upper end of collection device 100 and provide one or more inlet ports 128 for collection device 100 and configured to receive lengths of tubing 130** which may be configured as aspirational tubing, inlet tubing for saline, or other types of tubing.

As further shown in FIGS. 1-7, collection device 100 may further include a lower sectional component or insert 112 disposed within the interior space 108 and dividing interior space 108 into an upper region **108*a* and a lower region 108*b*. Depending on the particular embodiment of collection device 100, insert 112 functions to provide a shelf 114 within the conical collection device, and may be removably or fixed securely to the remainder of collection device 100 or integrally formed with the remainder of collection device 100. According to one embodiment of the present invention, insert 112 may be formed separately from the remainder of the collection device 100 and inserted therein. According to another embodiment, insert 112 that provides the shelf 114 is integrally formed with the inside perimeter of the holding device as part of collection device 100**.

As shown in FIGS. 1-7, insert 112 may include a top divider wall 114 intermediately positioned along the height of sidewall 102 and extending horizontally across sidewall 102. Top divider wall 114 may engage perimeter sidewall 102 around the entire perimeter of collection device 100 and form a physical barrier separating interior space 108 into its upper and lower regions **108*a* and 108*b*. Insert 112 may further include a conical-shaped cavity 116 defined into upper divider wall 114 and extending downward therefrom. Conical-shaped cavity 116 can include an upper circular opening 118 and a downwardly-depending conical sidewall 120 extending toward bottom panel 110 of collection device 100**.

Figure 2:
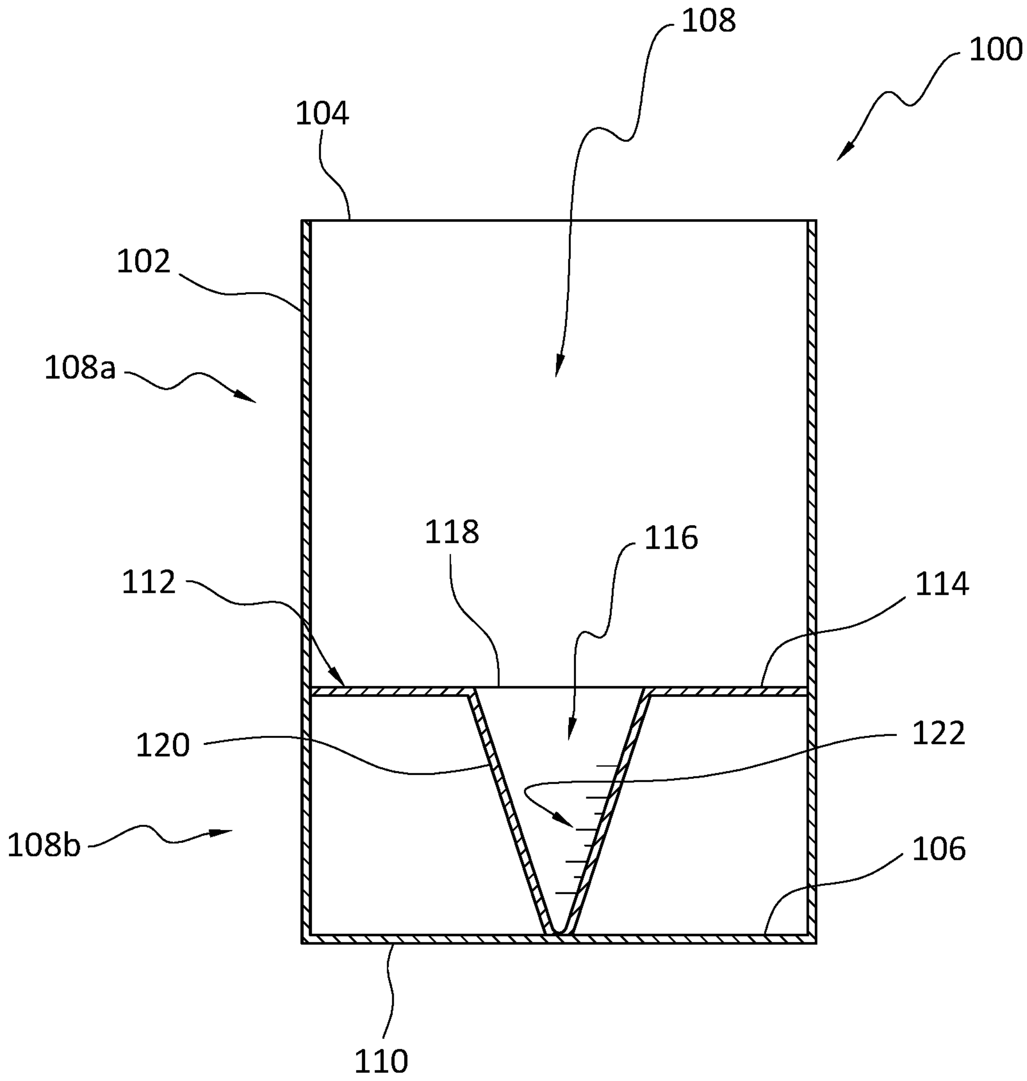
FIG. 2 is a schematic sectional view of the collection device of FIG. 1 taken along line 2-2 in the direction of the arrows.
Figure 3:
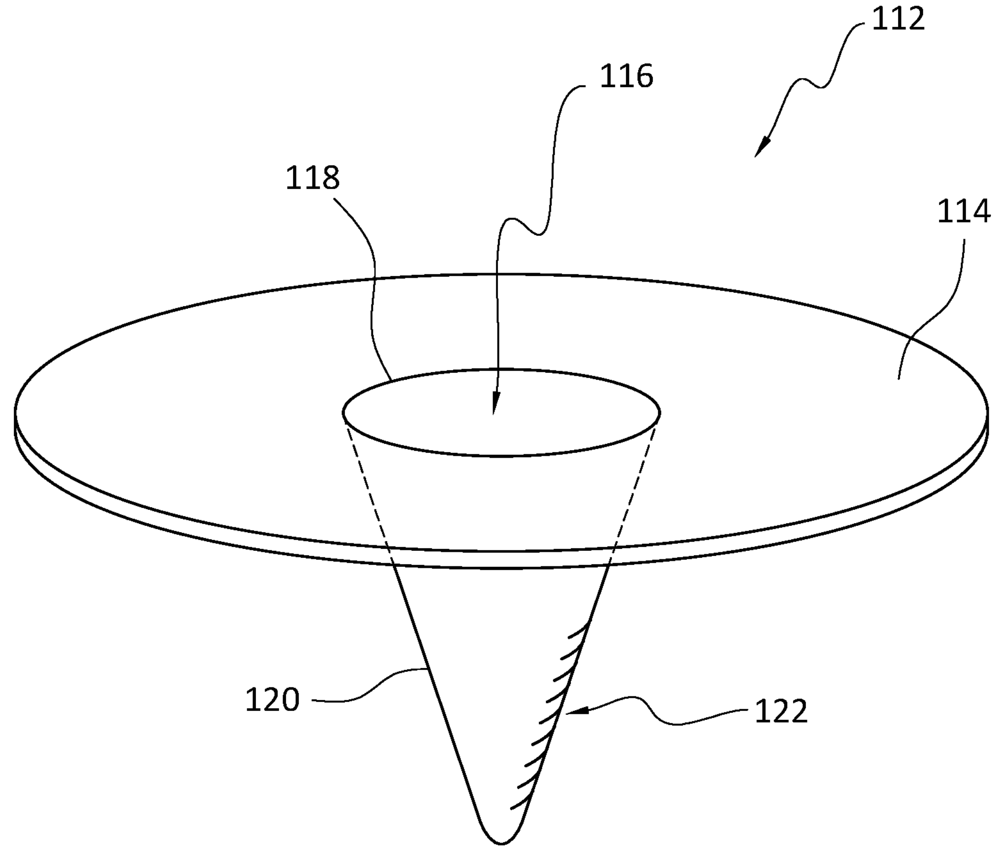
FIG. 3 is a schematic partial perspective view of an insert for use in the collection device of FIG. 1.

As best shown in FIGS. 1-3, according to one embodiment, conical-shaped cavity 116 may have a substantially smaller diameter than perimeter sidewall 102 (and upper divider wall 114) and may be centrally located within the interior of upper divider wall 114. Upper divider wall 114 may also have a slightly angled slope that extends at a downward angle toward conical-shaped cavity opening 118 in order to facilitate RBC sedimentation into conical-shaped cavity 116 (as described in greater detail below). In such an embodiment, conical-shaped cavity opening 118 is at an elevation slightly lower than the elevation of the outer perimeter edge of upper divider wall 114 where insert 112 engages sidewall 102 of collection device 100. It is also recognized that upper divider wall 114 may have any suitable arrangement or orientation in other embodiments of the present invention.

Figure 5:
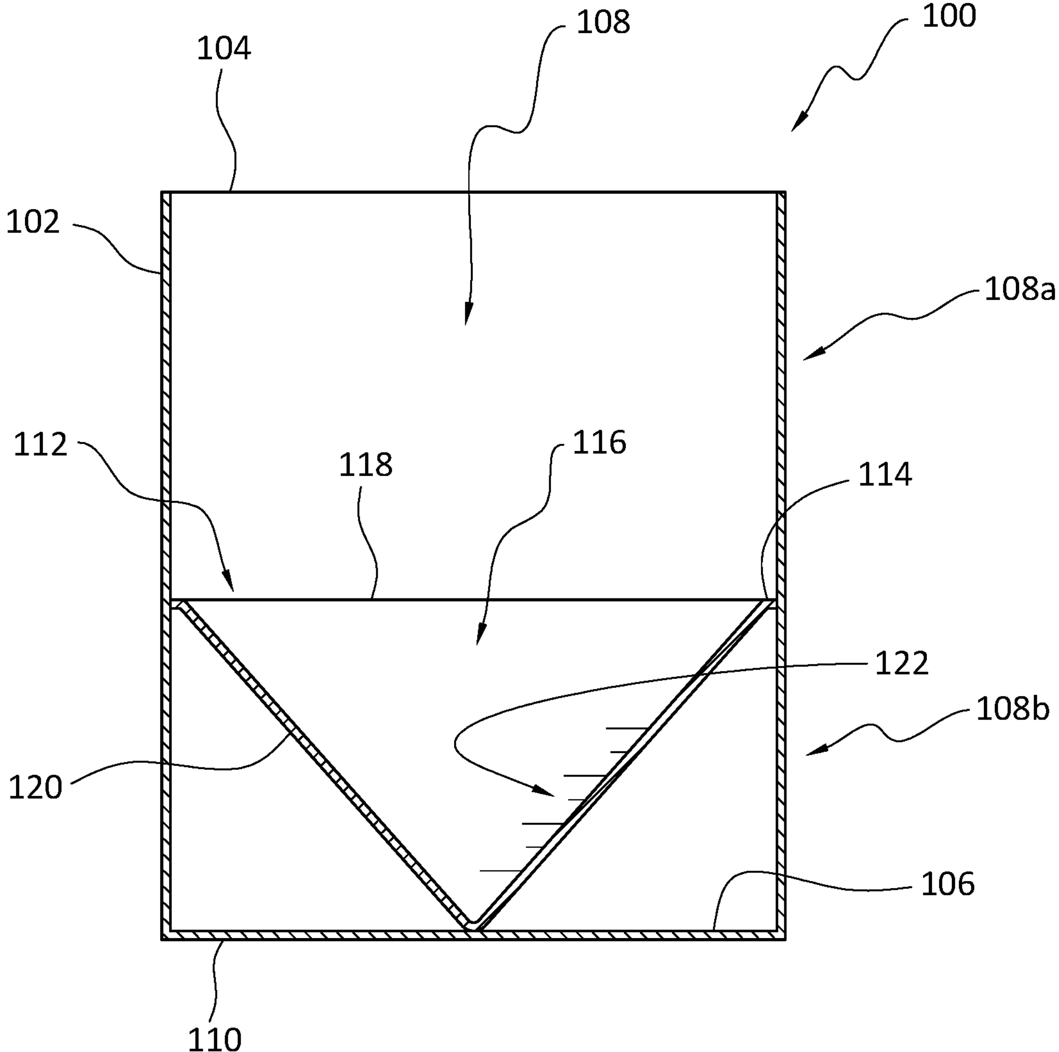
FIG. 5 is a schematic sectional view of the collection device of FIG. 4 taken along line 5-5 in the direction of the arrows.
Figure 6:
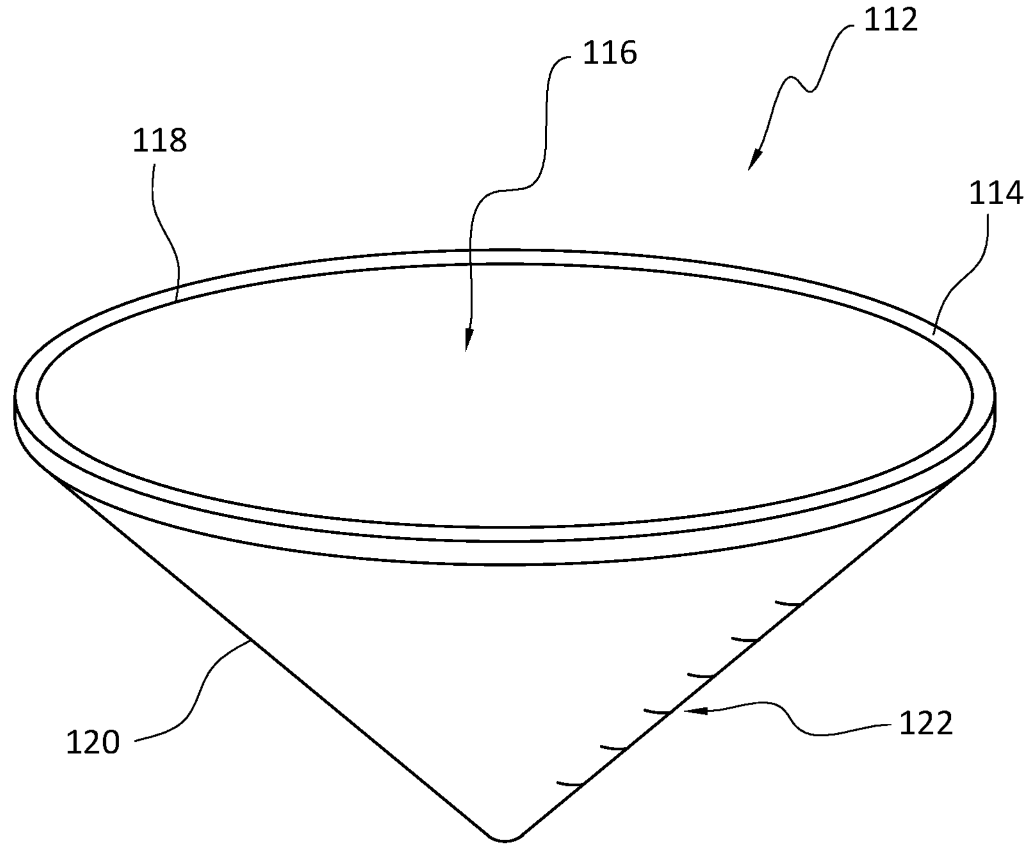
FIG. 6 is a schematic partial perspective view of an insert for use in the collection device of FIG. 4.

As best shown in FIGS. 4-6, according to another embodiment, conical-shaped cavity 116 may extend across all or a substantial portion of insert 112 and upper divider wall 114. As shown in FIGS. 4-6, conical-shaped cavity opening 118 may have a diameter substantially equal to or slightly less than upper divider wall 114, which engages perimeter sidewall 102 of collection device 100 in order to form the physical barrier separating interior space 108 into its upper and lower regions **108*a* and 108*b***.

As best shown in FIGS. 3 and 6, conical-shaped cavity 116 may include graduated markings in the form of a blood indicator panel (BIP) 122 positioned along the height of conical sidewall 120. Blood indicator panel 122 can extend completely or partially around conical sidewall 120 to provide a visual indication of the amount of blood and/or other fluids that have collected in conical-shaped cavity 116. In certain embodiments, blood indicator panel 122 may correspond to a volumetric amount (such as a volume of RBCs settled to the bottom of collection device 100). Blood indicator panel 122 may also be calibrated to correspond to a volume of blood contained within collection device 100 (based on a sedimented RBC volume as described in greater detail below). Collection device 100 may also include a fluid level panel 124 provided along the height of perimeter sidewall 102 in order to indicate the amount of total fluid or contents in the upper region **108*a* of collection device 100 (see FIG. 4). Collectively panels 122 and 124 may be used to identify the amount of blood and/or other fluids collected within the conical-shaped cavity 116 specifically and the overall collection device 100** generally.

Collection device 100 may be constructed from any suitable material, including plastic, glass, polymer-based material or other suitable material or any combination thereof. Collection device 100 may be sufficiently transparent or at least opaque so as to permit the visual detection of a level of material, such as sedimented RBCs, within collection device 100 and conical-shaped cavity 116.

Example 2—Use of RBC Flocculants with the Collection Device

According to certain embodiments, collection device 100 may be used with a RBC flocculent that facilitates the sedimentation of RBCs within the liquid provided into collection device 100. The particular RBC flocculant used with collection device 100 may be any suitable flocculant currently known or hereinafter developed. Non-limiting examples of potentially suitable flocculants may include: Polydiallyldimethylammonium chloride (PolyDADMAC); Polyethylenimine (PEI); Polyacrylamide (PAM); non-polymeric flocculants such as HCl and other acids; and the like. The RBC flocculant may further be used within collection device 100 in any suitable form, including without limitation, in solid form, in an aqueous solution, as a water-in-oil emulsion, or as a dispersion in water.

Normally, in the absence of a flocculant, the RBC sedimentation rate, or erythrocyte sedimentation rate (ESR) is relatively low, or not detectable to the unaided eye. As a result, it may take many hours or even days for RBCs to settle within the collection device 100 without centrifugation at room temperature in the absence of a flocculant. In the presence of an RBC flocculant, such as the RBC flocculant polyDADMAC, the RBC settlement rate can increase significantly. In the presence of an RBC flocculant, RBC sedimentation can occur in less than about 20 minutes, and formed a stable RBC sedimentation volume that was readily visible to the unassisted eye.

The RBC flocculant used in collection device 100 may be disposed within interior space 108 of collection device 100 in any suitable manner such that when a fluid potentially containing blood is inserted into collection device 100, the RBC flocculant may operate to facilitate the efficient sedimentation of RBCs within the fluid to determine an estimated blood volume as described herein.

Figures 8, 9:
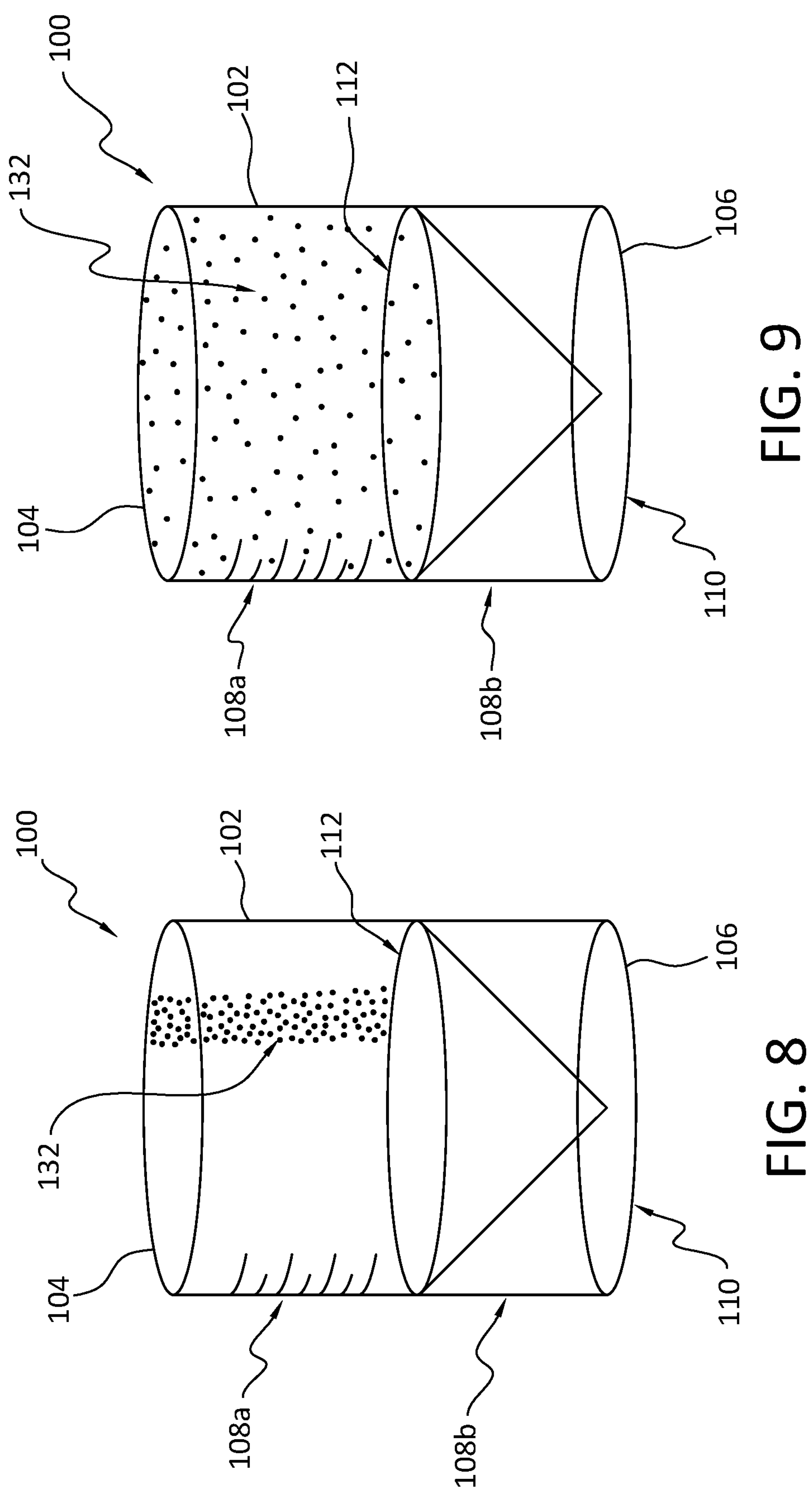
FIG. 8 is a schematic perspective view of a collection device for determining the amount of blood volume within a volume of liquid and having a RBC flocculant layer applied therein in accordance with one embodiment of the present invention.
FIG. 9 is a schematic perspective view of a collection device for determining the amount of blood volume within a volume of liquid and having a RBC flocculant layer applied therein in accordance with another embodiment of the present invention.

According to one embodiment, the RBC flocculant may be applied to the sidewall 102 of collection device 100 in the form of a vertical flocculant band 132 (see FIG. 8). The width of band 132 can be based, at least in part, on the diameter of collection device 100 in order to optimize the concentration of RBC flocculant to volume of liquid within collection device 100. According to one embodiment, flocculant band 132 may have a one-inch width; however, band 132 may have any other desired width and may even have a non-uniform width along the height of sidewall 102 of collection device 100. Vertical flocculant band 132 may be applied to sidewall 102 in any suitable manner, such as by brushing, spraying, misting, taping or otherwise adhering the flocculant comprising band 132 to sidewall 102 of collection device 100.

According to an alternative embodiment (see FIG. 9), the RBC flocculant may be applied to the interior space 108 of collection device by applying a uniform (or non-uniform) coating of flocculant to a portion of or the entirety of interior space 108 of collection device 100. The flocculant coating may be applied in any suitable manner, including without limitation, using ultrasound atomization technology. In this embodiment, the applied flocculant may form essentially a flocculant band 132 that extends around the entirety of sidewall 102 of collection device 100.

In each configuration, the flocculant band or coating 132 extends upward along sidewall 102 and as a result, only the portion of flocculant band 132 that immersed by the fluid within collection device 100 is dissolved/released into the fluid to cause RBC sedimentation. The flocculant band or coating 132 may further be applied to the insert 112 and/or conical-shaped cavity 116 in selected embodiments. In this manner, the flocculant band 132 may allow for a controlled release of flocculant proportional to the volume of fluid (i.e., blood, saline, etc.) in collection device 100.

Example 3—Methods of Using the Collection Device of the Present Invention for Estimating Blood Loss Collection device 100 may be used in connection with one or more methods for determining the amount of blood in a volume of liquid, including without limitation, determining the amount of blood loss of a patient during a surgical or other operating procedure. According to one method of the present invention, collection device 100 may be provided with an appropriate amount of RBC flocculant provided therein. The volume of liquid may then be inserted into the interior 108 of collection device 100. As a result of the RBC flocculant within collection device 100, the RBCs contained within any blood present the volume of liquid will settle toward the lower region 108*b* of collection device 100 through sedimentation and gravity. This process may be accomplished in less than an hour and as even as soon as 5-30 minutes after the volume of liquid is inserted into the collection device 100. During the sedimentation process, the RBCs within the volume of liquid with settle into the conical-shaped cavity 116 within collection device 100. After an appropriate amount of time as elapsed for stable sedimentation of RBCs within the volume of liquid, a settled RBC volume can be estimated using the graduated markings or BIP panel 122. These graduated markings 122 may be calibrated to provide a blood volume approximation contained within the volume of liquid and/or the blood volume approximation can be obtained based on the RBC volume using various formulas and methods. According to certain embodiments, the volume of blood may be determined using the teachings set forth in U.S. Pat. No. 10,401,347, the entire disclosure of which is incorporated herein by reference. According to certain embodiments, calibration of the graduated markings 122 to display the total blood volume (or blood loss volume) based on the volume of settled RBCs, the subject's hematocrit (Hct) value (or an average Hct determined from a number of similar subjects), and a packing ratio η, according to the following formula: $V_b=V_m/(Hct\times\eta)$, where $V_b$ is the total blood volume, $V_m$ is the sedimented RBC volume, Hct is the patient's calculated hematocrit, and η is the packing ration (which may be calculated based on the aspect ratio of the collection device 100 and one or more other variables). Any other suitable method for calibrating the graduated markings or BIP panel 122 may also be suitably used in accordance with the present invention.

Example 4—Methods for Estimating Blood Loss in Small Amounts of Fluid Volume Collection device 100 may be sized and configured for use in situations where a small amount of blood volume must be determined from a volume of fluid. In a typical operating room setting, smaller volumes of fluid containing blood and other materials (tissue, urine, non-blood fluid, etc.) will be aspirated from a surgical field. The aspiration of these fluids results in an undetermined loss of blood from the patient. Collection device 100 according to the present invention may be sized and configured to accommodate the estimation of blood loss in these small, sometimes critical, volumes of collected fluid. According to one embodiment, collection device 100 may be sized to hold approximately 100 ml of fluid within interior space 108 of collection device 100. The interior space 108 of collection device 100 may then be provided with a RBC flocculant, such as polyDADMAC, and can be especially useful for determining blood volume in small amounts of collected fluid. This embodiment of collection device 100 may be used, for example, in pediatric applications (infant) as well as in low volume critical fluid collection procedures.

Example 5—Human Pediatric Applications for Use in Estimating Blood Loss

Collection device 100 and the methods described in accordance with the present invention may be used for efficient measurement of blood loss in a pediatric patient. As used in the present embodiment, a pediatric patient may be defined as an individual up to 12 years of age having a body weight of up to 70 to 80 pounds.

A person's total blood volume (TBV) is related to body weight. The TBV of a child is around 75-80 ml/kg and is higher in the neonatal period (from 85 ml/kg it rises to a peak of 105 ml/kg by the end of the first month and then drops progressively over ensuing months). Thus, the TBV of a 3.5-kg 2-week-old will be about 350 ml while that of a 10-kg 15-month-old will be about 800 ml.

Because of the much reduced total volume of blood in a pediatric patient, it is especially important to provide a blood collection and blood loss estimation system and device that are designed for estimating blood loss accurately from a smaller volume of blood collected from a pediatric patient. Accordingly, collection device 100 may be specifically designed for pediatric blood loss estimation therefore crafted as a container having the herein described flocculant and canister demarcations with a total volume capacity of less than 1000 ml, such as about 500 ml or even about 250 ml, in the case of an infant or neonate.

A large acute loss of blood volume in a pediatric patient may compromise the circulation, and therefore blood loss should be carefully monitored so as to be able to detect a volume of blood loss of about 12% of the TBV (around 10 ml/kg) of the specific pediatric patient, assuming the child is in a stable condition and has a normal blood hemoglobin (Hb) level at the beginning of a procedure.

By way of example, collection device 100 may, in some embodiments, have a capacity of 250 mLs. The collection device 100 according to such an embodiment would preferably provide an appropriate aspect ratio of D:H for a typical pediatric blood loss volume. The D (diameter) of the collection device 100 would typically be between 2 and 3 inches, and have an H (height) of about 2 inches to about 3 inches. With these smaller dimensions, a collected blood loss volume would provide a reasonably rapid yet monitorable sedimentation rate of RBCs so as to alert an attending physician if an amount of blood loss has reached a volume where transfusion to the pediatric patient is in order. It would be preferred that a sedimentation rate would be achieved that provides for RBC sedimentation within 15 minutes of blood collected in the collection device.

As described herein, collection device 100 may include a conical-shaped cavity 116 located within a lower interior region 108*b* of the interior 108 of collection device 100. The flocculant may be provided within the collection device 100 either at the time of the surgical intervention event, or may be provided as a pretreatment to the canister (such as by a spray coating) as described above.

The amount of flocculant to be added to a 250 ml collection device 100 according to certain embodiments may be about 50 mg to about 150 mg, or about 125 mg, or an amount sufficient to achieve at least a 0.3%, 0.4% or 0.75% of total volume of the solution.

According to one example, the following average total blood volume in a pediatric group of patients may be used in calculating when a 12% or greater blood loss has occurred. An average hematocrit value may also be calculated for the class/group (premature neonate, full term neonate, infant) of pediatric patients, and a marking provided alongside one axis of the collection device 100, of average hematocrit values for these patient groups, so as to provide a ready visual reference for the attending physician or anesthesiologist to refer to and compare as against the hematocrit obtained for the patient undergoing the procedure:

Premature Neonates 95 ml/kg
Full Term Neonates 85 ml/kg
Infants 80 ml/kg

The total approximation of blood volume may be calculated by the formula described herein by using the average hematocrit of for a human child of a particular weight range and/or age, or for a human adult male or adult female, the $V_m$ (observable settled RBC volume in ml), and the packed ratio value (n) determined for human blood. With multiple human blood sample assessments of settled RBC volume ($V_m$) and Hct information, a visual blood volume indicator panel 122 to be located along the vertical axis of the conical-shaped cavity 116 may be prepared for the human, and especially for a pediatric human model. This may provide an immediately visually discernable approximation of blood volume in volumes less than about 250 ml, contained in a biological fluid containing human blood. The development of a collection device 100 having a Blood Indicator Panel 122 for human blood volume assessment in a liquid, and especially for assessing small volumes of human blood loss, may be developed by one of ordinary skill in the art given the teachings provided herein, without more than a routine and ordinary amount of trial and error.

Example 6—Veterinary Applications for Use in Estimating Blood Loss

Collection device 100 and the methods described in accordance with the present invention may be used for efficient measurement of blood loss in a veterinary subject. As used in the present embodiment, a veterinary subject may be defined as a domestic or companion animal, such as a dog, cat, horse, rabbit, bird, or guinea pig, for example.

Domestic animals have blood volumes of 7%-9% of their body weight. For example, a 25-kg dog has a total blood volume of about 2 liters. In comparison, an adult human has a total blood volume of about 5 liters. Given the much lower total blood volume of domestic animals, important to provide a blood collection and blood loss estimation system and device that are designed for estimating blood loss accurately from a smaller volume of blood collected from a veterinary subject. Accordingly, collection device 100 may be specifically designed for veterinary blood loss estimation therefore crafted as a container having the herein described flocculant and canister demarcations with a total volume capacity of less than 2 L, for example. As described herein, collection device 100 may include a conical-shaped cavity 116 located within a lower interior region 108*b* of the interior 108 of collection device 100. The flocculant may be provided within the collection device 100 either at the time of the surgical intervention event, or may be provided as a pretreatment to the canister (such as by a spray coating) as described above.

Example 7—Blood Loss Collection Kit Using the Collection Device

The collection device 100 of the present invention may be configured as a collection kit or system for receiving a volume of liquid from a patient and potentially containing blood and determining the amount of blood loss of the patient in accordance with one embodiment of the present invention. As best shown in FIG. 7, collection device 100 may be constructed and configured in as described herein with a conical-shaped cavity 116 and a blood indicator panel 122. According to this embodiment and as further shown in FIG. 7, collection device 100 may further include a lid or top panel 126, a pair of inlet ports 128 defined though lid 126 and lengths of tubing 130 suitable connected to inlet ports 128. One length of tubing 130 may be configured for aspiration from the patient (or operating site) to the interior 108 of collection device 100 and the second length of tubing 130 may be configured for adding saline into the collection device 100. Upon receiving a volume of fluid (via lengths of tubing 130) within collection device 100, the total blood loss volume may be determine using the blood indicator panel 122 and the methods described herein.

The examples set forth above are provided to give those of ordinary skill in the art a complete disclosure and description of how to make and use the embodiments of the methods for prediction of the selected modifications that may be made to a biomolecule of interest, and are not intended to limit the scope of what the inventors regard as the scope of the disclosure. Modifications of the above-described modes for carrying out the disclosure can be used by persons of skill in the art, and are intended to be within the scope of the following claims.

It is to be understood that the disclosure is not limited to particular methods or systems, which can, of course, vary. It is also to be understood that the terminology used herein is for the purpose of describing particular embodiments only, and is not intended to be limiting.

A number of embodiments of the disclosure have been described. Nevertheless, it will be understood that various modifications may be made without departing from the spirit and scope of the present disclosure. Accordingly, other embodiments are within the scope of the following claims.

What is claimed is:

1. A conical collection device configured to measure a volume of blood in a volume of 10 mls or less of a fluid, wherein the conical collection device comprises:

a shelf having an outside perimeter configured to fit up against an inside perimeter of a holding device for a conical-shaped fluid collection cone, wherein the shelf comprises an opening configured to receive an open top end of the conical-shaped fluid collection cone; and a conical-shaped collection reservoir, said conical-shaped collection reservoir comprising:

a top end configured to fit within the opening of the shelf;

a length;

an interior surface;

a decreasing perimeter starting at the top end and terminating in a bottom apex of the conical-shaped collection reservoir, and a series of markings along the length of the conical-shaped collection reservoir corresponding to sedimented red blood cells in the conical-shaped collection reservoir, the sedimented red blood cells corresponding to a calculated red blood cell volume in the conical-shaped collection reservoir.

2. The conical collection device of claim 1, wherein the interior surface of the conical-shaped fluid collection reservoir comprises a red blood cell flocculant.

3. The conical collection device of claim 2, wherein the red blood cell flocculant is polyDADMAC.

4. The conical collection device of claim 1, wherein the graduated markings are provided along the interior surface or an exterior surface of the conical-shaped collection reservoir.

5. The conical collection device of claim 1, wherein the shelf is integrally formed with the inside perimeter of the holding device.

6. The conical collection device of claim 1, configured to be removably inserted into the holding device.

7. The conical collection device of claim 1, wherein the conical-shaped collection is transparent.

* * * * *